(12) United States Patent
Hinchey

(10) Patent No.: US 7,390,655 B2
(45) Date of Patent: Jun. 24, 2008

(54) PROMOTER MOLECULES FOR USE IN PLANTS

(75) Inventor: Brendan Hinchey, Mystic, CT (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 11/387,036

(22) Filed: Mar. 21, 2006

(65) Prior Publication Data

US 2007/0226816 A1    Sep. 27, 2007

(51) Int. Cl.
*C12N 15/82* (2006.01)
*C12N 15/00* (2006.01)
*C07H 21/00* (2006.01)
*A01H 5/10* (2006.01)

(52) U.S. Cl. ............. 435/320.1; 800/285; 800/286; 800/278; 800/298; 435/468; 435/410; 536/24.1

(58) Field of Classification Search .......... None
See application file for complete search history.

(56) References Cited

U.S. PATENT DOCUMENTS

| 5,686,649 A | * | 11/1997 | Chua et al. ........... | 800/285 |
| 7,091,398 B2 | | 8/2006 | Dhugga et al. ........ | 800/284 |
| 2004/0034888 A1 | | 2/2004 | Liu et al. ............ | 800/289 |

FOREIGN PATENT DOCUMENTS

| WO | WO 2004/101741 | 11/2004 |
| WO | WO2004101741 A2 * | 11/2004 |

OTHER PUBLICATIONS

Maiti et al 1997, Transgen. Res., 6:143-156.*
Donald et al 1990, EMBO J. 9:1717-1726.*
Benfey et al, 1990, Science 250:959-966.*
Kim et al, 1994, Plant Mol. Biol. 24:105-117.*
Hood et al., "Molecular characterization of maize extensin expression," *Plant Molecular Biology*, 23:685-695, 1993.
Raz et al., "The sequence of a hydroxyproline-rich glycoprotein gene from *Sorghum vulgare*," *Plant Molecular Biology*, 16:365-367, 1991.
GenBank Accession No. AJ131535, Nov. 14, 2006.
GenBank Accession No. X63134, Nov. 14, 2006.
GenBank Accession No. CG357706, Aug. 26, 2003.
GenBank Accession No. CC607410, Jun. 18, 2003.
Menossi et al., "Promoter tissue specific activity and ethylene control of the gene encoding for the maize hydroxyproline-rich glycoprotein in maize cells transformed by particle bombardment," *Plant Sci.*, 125:189-200, 1997.
Wycoff et al., "Stress Activation of a bean hydroxyproline-rich glycoprotein promoter is superimposed on a pattern of tissue-specific developmental expression," *Plant Physiol*, 109:41-52, 1995.
GenBank Accession No. X64173, Jun. 29, 1992.
Guo et al., "mRNA accumulation and promoter activity of the gene coding for a hydroxyproline-rich glycoprotein in oryza sativa," *Plant Mol. Biol.*, 25:159-165, 1994.
International Search Report, PCT/US06/10560, Sep. 13, 2007.

* cited by examiner

*Primary Examiner*—Russell P. Kallis
*Assistant Examiner*—Brent T Page
(74) *Attorney, Agent, or Firm*—Sonnenschein Nath & Rosenthal LLP

(57) ABSTRACT

The present invention provides DNA molecules isolated from corn and sorghum plants that are useful for expressing transgenes in plants. The present invention also provides expression constructs containing the DNA molecules useful for expressing transgenes in plants. The present invention also provides transgenic plants and seeds containing the DNA molecules useful for expressing transgenes in plants.

10 Claims, 1 Drawing Sheet

SEQUENCE LISTING

```
<160> NUMBER OF SEQ ID NOS: 2

<210> SEQ ID NO 1
<211> LENGTH: 1406
<212> TYPE: DNA
<213> ORGANISM: Zea mays

<400> SEQUENCE: 1
gattggtaga atccgacggg ttgataccce tgcaatcgta gcgtgatgag ggtgtgaatg      60
ttgccgatgt gtggacttcg aggaaatgat agcccctgga tgccgagata gccgaagtcg     120
aggtggtcgt ggtcgggaga cacgcagcag tagcctattc tttggtaggg gtcgatgttc     180
aagcgtcaac gatcggctgg gcgacataaa aattagcacc agggtgacct tcttgcttct     240
tcgatcgtct ggacgtcgag gagccccgcg gcagcgcacg cgtctgcacc gttatggtgg     300
ccgcgctcgc gatggaatag aagggtaat gatggatccg gccaggaagg ccacgacatc      360
gacggatcca accggcaaga cggcgatccg gttaaataga cgacggatct agctgggaag     420
gtagactcta tattaaatga ggttgtacat gccctaataa ctttataaat ctaatttatt     480
cagaggcaag gtagtagtat tatctttccc aacggatagt tatctgatct gccgttcagc     540
ttgatcgata actttataaa tctaatttat tcagaggccg gcggcagcgc acacgtctgc     600
accagtaatg ttagccgcgc ctgtggcgta atagaagggg taacgatgga tccgaccaga     660
aaggcctcga catcgacgga tccagacggc gatccggtca aagagacgac gaatctagcc     720
gagaaggtag atctctcgag agagttcata ttaaatgatg ttgtacatgc cataataact     780
ctataaatct aatttattca taggcgaagg tagtagtatt atctttccca gcggatcgtt     840
atctgatctg ccgttcagct tgatcgatcc acgtcgtttg atctcggcga gcagcacatg     900
gcggctcttc ttgtgtacag gtctcactct ctgctacttc agtgcaaggc ggagtgaacg     960
cacacaataa cgtgagtatt gtgggaacta ccttgtagat gcaaacgatg taaatccacc    1020
tgctccacca agtgcccgcc cggctctatc cattccattc gtcaacatgc aggttcaaga    1080
ctggcccgtg ctggaccagt gagcggtgcc ggtggacccc aatgcaagcg aagcgagtga    1140
ccatcgggga agcctcccgt gctgccccca catggcttgc ctgaatgcct ctctctcgcc    1200
gcagtgccct ctctctctcc tcctcctctc cgtcgaaggg cgtcacgaga gcccagaggg    1260
catccgaggc ccccacccca ccccttcctc ccgtgtatat aagcagtggc agggtgagcg    1320
tctctcctca gaccaccact gcgccatggc cagctagagc caaccagaag agcttgcagt    1380
tactgagagt gtgtgagaga gagagg                                        1406
```

-continued

```
<210> SEQ ID NO 2
<211> LENGTH: 763
<212> TYPE: DNA
<213> ORGANISM: Sorghum sp.

<400> SEQUENCE: 2
ccggccgcca tggcggccgc gggaaattcg attccacgga gttctagatt tggttttgc        60 ggtgaactaa acaaggccat atattagtgt gctgtgtttc ccctacgaa gcattgtgga       120 gtcgtgcttg atccacgtcg tttgatctgg gcgaggtgca caaacgtcac atggctcttc      180
ttgctacttc agtgcaaagg gagtgtatgc atgcacacaa taatgcggcc tgcgtctgtg      240
tacggtagaa aaatacttta tacaggatat gcaacgacgt gaatgctgca cctgccccct     300
gcccctgccc ctgcccgccc tagtagctat tcacggctct atccattcca ttgccgtgcg     360
tcaacaggtc cagactggcc cgggtccaag cgagtgacca acgcgggaag cctcccgtcc     420
ctccctcccc cacatgggac atggctgcct gatgaatgcc tctcgccgca ctgcccctgc     480
ccctgcccct gcccctgccc tcactccatc ggagggcggc ggcttcacga gagccgagca     540
ggacccagac ccagcgggca tccgaggccc ccaccccac cccaccccct tcctccgtgt      600
ataaaagcgg tgccaggggtg agcgtctctc ctcacactga ctgcaccaga acaagagctt    660
gagagtgaga gtgaggctgc agggaagtgt aatcactagt gaattcgcgg ccgcctgcag    720
gtcgaccata tgggagagct cccaacgcgt tggatgaagc tgg                       763
```

PROMOTER MOLECULES FOR USE IN PLANTS

This application claims the benefit of priority of U.S. Provisional Patent Application No. 60/663,817, filed Mar. 21, 2005, which is incorporated by reference in its entirety herein. Two copies of the sequence listing (Seq. Listing Copy 1 and Seq. Listing Copy 2) and a computer-readable form of the sequence listing, all on CD-ROMs, each containing the file named Silk-1.ST25.txt, which is 4,096 bytes (measured in MS-DOS) and was created on Mar. 21, 2006, are herein incorporated by reference.

FIELD OF THE INVENTION

The invention relates to the field of plant molecular biology and plant genetic engineering and to polynucleotide molecules useful for the expression of transgenes in plants.

BACKGROUND

While previous work has provided a number of regulatory elements useful to affect gene expression in transgenic plants, there is still a great need for novel regulatory elements with beneficial expression characteristics. In particular, there is a need for regulatory elements that are capable of directing expression of transgenes in transgenic crop plants at high levels and in particular tissues, organs, or during specific developmental stages of plant growth.

Useful regulatory elements can be isolated from genes having a desired pattern and/or level of expression of the gene. Silk of certain monocots such as maize plays an important role in many physiologically important processes such as determination of fertilization rate and susceptibility to insects or certain plant diseases. Regulatory elements from genes that are preferentially expressed in plant silk can be utilized for modifying plant phenotypes by expression transgene controlled by such elements. The hydroxyproline rich glycoprotein (HRGP) gene is one of many genes that is preferentially expressed in plant silk (Hood, E., Murphy, J. & Pendleton; Plant Molecular Biology; 23:685-695, 1993 and Raz, R., Cretin, C., Puigdomenech, P. & Martiez-Izquierdo, J.; Plant Molecular Biolgy; 16: 365-367, 1991). Corn and sorghum genes were used for isolating regulatory elements of the present invention to obtain a desired expression pattern of a transgene as presented here.

SUMMARY OF THE INVENTION

This invention provides promoters isolated from the regulatory region of HRGP gene from corn and sorghum having the nucleotide sequence of SEQ ID NO:1 and SEQ ID NO:2, and that are useful for expressing transgenes in plants. More specific aspects of the invention are isolated DNA molecules having promoter function and comprising (a) about 75 to about 1400 contiguous bases from SEQ ID NO:1, wherein said contiguous bases have from 80% to 100% sequence identity to at least one segment of SEQ ID NO: 1; (b) about 75 to about 750 contiguous bases from SEQ ID NO:2, wherein said contiguous bases have from 80% to 100% sequence identity to at least one segment of SEQ ID NO:2; (c) a derivative of a HRGP promoter with SEQ ID NO:1 or SEQ ID NO:2; or (d) a fragment of HRGP promoter with SEQ ID NO: 1 or SEQ ID NO:2.

Another embodiment of the invention provides recombinant DNA constructs comprising any of the promoters of this invention operably linked to DNA to be transcribed. In other embodiments, the invention provides transgenic plants, plant parts, and seed containing the promoter.

DETAILED DESCRIPTION OF THE INVENTION

Figure 1:
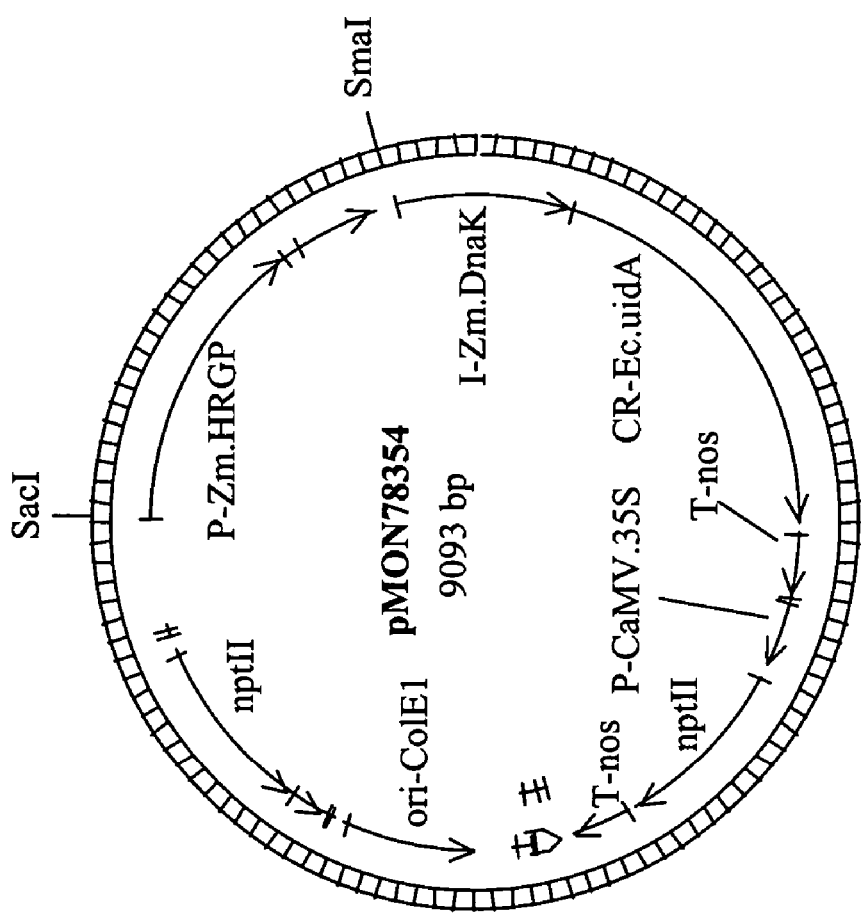
FIG. 1 represents plasmid map of pMON78354.

As used herein, "promoter" means a region of DNA sequence that is essential for the initiation of transcription of DNA, resulting in the generation of an RNA molecule that is complimentary to the transcribed DNA; this region may also be referred to as a "5' regulatory region." Promoters are located upstream of the coding sequence to be transcribed and have regions that act as binding sites for RNA polymerase and work with other factors to promote RNA transcription. More specifically, basal promoters in plants comprise canonical regions associated with the initiation of transcription, such as CAAT and TATA boxes. The TATA box element is usually located approximately 20 to 35 nucleotides upstream of the initiation site of transcription. The CAAT box element is usually located approximately 40 to 200 nucleotides upstream of the start site of transcription. The location of these basal promoter elements result in the synthesis of an RNA transcript comprising nucleotides upstream of the translational ATG start site. The region of RNA upstream of the ATG is commonly referred to as a 5' untranslated region or 5' UTR. It is possible to use standard molecular biology techniques to make combinations of basal promoters, that is, regions comprising sequences from the CAAT box to the translational start site, with other upstream promoter elements to enhance or otherwise alter promoter activity or specificity.

As used herein, "promoter activity" characterizes a DNA sequence that initiates transcription of RNA from adjacent downstream DNA.

Promoters are involved in recognition and binding of RNA polymerase II and other proteins such as transcription factors (trans-acting protein factors that regulate transcription) to initiate transcription of an operably linked gene. Promoters may themselves contain sub-elements such as cis-elements or enhancer domains that effect the transcription of operably linked genes.

The promoters of this invention may be altered to contain "enhancer DNA" to assist in elevating gene expression. As is known in the art, certain DNA elements can be used to enhance the transcription of DNA. These enhancers often are found 5' to the start of transcription in a promoter that functions in eukaryotic cells, but can often be inserted upstream (5') or downstream (3') to the coding sequence. In some instances, these 5' enhancer DNA elements are introns. Among the introns that are useful as enhancer DNA are the 5' introns from the rice actin 1 gene (see, e.g., U.S. Pat. No. 5,641,876), the rice actin 2 gene, the maize alcohol dehydrogenase gene, the maize heat shock protein 70 gene (see, e.g., U.S. Pat. No. 5,593,874), the maize shrunken 1 gene, the light sensitive 1 gene of *Solanum tuberosum*, and the heat shock protein 70 gene of *Petunia hybrida* (see, e.g., U.S. Pat. No. 5,659,122).

As used herein, the term "percent sequence identity" refers to the percentage of identical nucleotides between two segments of a window of optimally aligned DNA. Optimal alignment of sequences for aligning a comparison window are well-known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components that are shared by the two aligned sequences divided by the total number of components in the reference sequence segment, i.e., the entire reference sequence or a smaller defined part of the reference sequence. Percent sequence identity is represented as the identity fraction times 100. The comparison of one or more DNA sequences may be to a full-length DNA sequence or a portion thereof, or to a longer DNA sequence.

DNA Isolation and Modification Methods

Any number of methods well known to those skilled in the art can be used to isolate fragments of a DNA molecule disclosed herein. For example, PCR (polymerase chain reaction) technology can be used to amplify flanking regions from a genomic library of a plant using publicly available sequence information. A number of methods are known to those of skill in the art to amplify unknown DNA sequences adjacent to a core region of known sequence. Methods include but are not limited to inverse PCR (IPCR), vectorette PCR, Y-shaped PCR, and genome walking approaches. DNA molecule fragments can also be obtained by other techniques such as by directly synthesizing the fragment by chemical means, as is commonly practiced by using an automated oligonucleotide synthesizer. For the present invention, the DNA molecules were isolated by designing PCR primers based on available sequence information.

Derivatives of the DNA molecules disclosed herein may include, but are not limited to, deletions of sequence, single or multiple point mutations, alterations at a particular restriction enzyme site, addition of functional elements, or other means of molecular modification which may enhance, or otherwise alter promoter expression. Techniques for obtaining such derivatives are well-known in the art (see, for example, J. F. Sambrook, D. W. Russell, and N. Irwin (2000) *Molecular Cloning: A Laboratory Manual, 3rd edition Volumes* 1, 2, and 3. Cold Spring Harbor Laboratory Press, hereafter referred to as Sambrook et al., 2000, incorporated by reference herein). For example, one of ordinary skill in the art may delimit the functional elements within the promoters disclosed herein and delete any non-essential elements. Functional elements may be modified or combined to increase the utility or expression of the sequences of the invention for any particular application. The means for mutagenizing or creating deletions in a DNA segment encoding a HRGP promoter sequence of the current invention are well-known to those of skill in the art and are disclosed in detail, for example, in U.S. Pat. No. 6,583,338, which is incorporated herein by reference in its entirety.

Those of skill in the art are familiar with the standard resource materials that describe specific conditions and procedures for the construction, manipulation, and isolation of macromolecules (e.g., DNA molecules, plasmids, etc.), as well as the generation of recombinant organisms and the screening and isolation of DNA molecules.

DNA Constructs

As used herein, the term "DNA construct" means an artificially assembled DNA segment to be transferred into one or more cell or target tissue of a desired organism. Typically, the construct will include a gene of particular interest, a marker gene, and appropriate control sequences.

As used herein, "operably linked" means the association of two or more DNA fragments in a DNA construct so that the function of one, e.g., protein-encoding DNA, is affected by the other, e.g., a promoter. For example, a promoter is operably linked to a gene of interest if the promoter regulates or mediates transcription of the gene of interest in a cell.

For the practice of the present invention, conventional compositions and methods for preparing and using constructs and host cells are well-known to one skilled in the art (see for example, Sambrook, et al., 2000).

Constructs of the present invention would typically contain a HRGP (also referred to as Silk-1) promoter element, with optional enhancer DNA, operably linked to transcribable DNA, e.g., for encoding a protein or a gene suppression RNA, and a polyadenylation site.

Thus, one embodiment of the invention is a polynucleotide molecule such as provided in SEQ ID NO:1 or SEQ ID NO:2, operably linked to a transcribable DNA molecule. The transcription of such a DNA molecule will be caused upon introduction of said construct into a plant cell or a plant at a level or in a tissue or developmental stage that is characteristic of SEQ ID NO:1 or SEQ ID NO:2 as shown in examples of the present disclosure. Such transcription of operably linked DNA molecules can be altered by adding or deleting other elements in a construct. In some cases, the transcribable DNA molecule comprises a protein-coding region of a gene, and the promoter provides for transcription of a fuictional MRNA molecule that is translated and expressed as a protein product. Constructs may also be constructed for transcription of antisense RNA molecules or other similar inhibitory RNA molecules in order to suppress expression of a specific gene of interest in a target host cell.

Thus, in one embodiment, a DNA molecule of the present invention as shown in SEQ ID NO:1 or SEQ ID NO:2 is incorporated into a construct such that a DNA molecule of the present invention is operably linked to a transcribable DNA molecule that provides for a selectable, screenable, or scorable marker. Markers for use in the practice of the present invention include, but are not limited to, transcribable DNA molecules encoding β-glucuronidase (GUS), green fluorescent protein (GFP), luciferase (LUC), proteins that confer antibiotic resistance, and proteins that confer herbicide tolerance. Useful antibiotic resistance markers, including those encoding proteins conferring resistance to kanamycin (nptII), hygromycin B (aph IV), streptomycin or spectinomycin (aad, spec/strep) and gentamycin (aac3 and aacC4) are known in the art. Herbicides for which transgenic plant tolerance has been demonstrated and the method of the present invention can be applied, include, but are not limited to: glyphosate, glufosinate, sulfonylureas, imidazolinones, bromoxynil, delapon, cyclohezanedione, protoporphyrionogen oxidase inhibitors, and isoxaflutole herbicides. DNA molecules encoding proteins involved in herbicide tolerance are known in the art, and include, but are not limited to, a DNA molecule encoding 5-enolpyruvylshikimate-3-phosphate synthase (EPSPS) described in U.S. Pat. No. 5,627,061, U.S. Pat. No. 5,633,435, U.S. Pat. No. 6,040,497, and U.S. Pat. No. 5,094, 945 for glyphosate tolerance, all of which are hereby incorporated by reference; a DNA molecule encoding bromoxynil nitrilase (Bxn) described in U.S. Pat. No. 4,810,648 for Bromoxynil tolerance, which is hereby incorporated by reference; a DNA molecule encoding phytoene desaturase (crtI) described in Misawa, et al., (1993) *Plant J.* 4:833-840 and Misawa, et al., (1994) *Plant J.* 6:481-489 for norflurazon tolerance; a DNA molecule encoding acetohydroxyacid synthase (AHAS, aka ALS) described in Sathasivan, et al. (1990) *Nucl. Acids Res.* 18:2188-2193 for tolerance to sulfonylurea herbicides; and the bar gene described in DeBlock, et al., (1987) *EMBO J.* 6:2513-2519 for glufosinate and bialaphos tolerance.

In one embodiment of the invention, a DNA molecule as shown in SEQ ID NO:1 or SEQ ID NO:2 is incorporated into a construct such that a DNA molecule of the present invention is operably linked to a transcribable DNA molecule that is a gene of agronomic interest, e.g., a gene that provides a desirable characteristic associated with plant morphology, physiology, growth and development, yield, nutritional enhancement, disease or pest resistance, herbicide resistance or environmental or chemical tolerance. The expression of a gene of agronomic interest is desirable in order to confer an agronomically important trait.

Alternatively, a transcribable DNA molecule can effect the above-mentioned phenotypes by encoding an RNA molecule that causes the targeted suppression of expression of an endogenous gene, for example via antisense, dsRNA, or co-suppression-mediated mechanisms. The RNA could also be a catalytic RNA molecule (i.e., a ribozyme) engineered to cleave a desired endogenous mRNA product. Thus, any DNA molecule that encodes a protein or MRNA that expresses a phenotype or morphology change of interest may be useful for the practice of the present invention.

Constructs of the invention are generally double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *Agrobacterium cells*, permits the integration of the T-DNA into the genome of a plant cell. The constructs also contain the plasmid backbone DNA segments that provide replication function and antibiotic selection in bacterial cells, for example, an *E. coli* origin of replication such as ori322, a broad host range origin of replication such as oriV or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, or LBA4404, however, other strains known to those skilled in the art of plant transformation can function in the present invention.

Transformed Plants And Plant Cells

As used herein, the term "transformed" refers to a cell, tissue, organ, or organism into which has been introduced a foreign DNA molecule, such as a construct. The introduced DNA molecule may be integrated into the genomic DNA of the recipient cell, tissue, organ, or organism such that the introduced DNA molecule is inherited by subsequent progeny. A "transgenic" or "transformed" cell or organism also includes progeny of the cell or organism and progeny produced from a breeding program employing such a transgenic plant as a parent in a cross and exhibiting an altered phenotype resulting from the presence of a foreign DNA molecule. A plant transformation construct containing a DNA molecule of the present invention may be introduced into plants by any plant transformation method. Methods and materials for transforming plants by introducing a plant expression construct into a plant genome in the practice of this invention can include any of the well-known and demonstrated methods including electroporation as illustrated in U.S. Pat. No. 5,384,253; microprojectile bombardment as illustrated in U.S. Pat. No. 5,015,580; U.S. Pat. No. 5,550,318; U.S. Pat. No. 5,538,880; U.S. Pat. No. 6,160,208; U.S. Pat. No. 6,399,861; and U.S. Pat. No. 6,403,865; *Agrobacterium*-mediated transformation as illustrated in U.S. Pat. No. 5,824,877; U.S. Pat. No. 5,591,616; U.S. Pat. No. 5,981,840; and U.S. Pat. No. 6,384,301; and protoplast transformation as illustrated in U.S. Pat. No. 5,508,184, all of which are hereby incorporated by reference.

Methods for specifically transforming dicots are well known to those skilled in the art. Transformation and plant regeneration using these methods have been described for a number of crops including, but not limited to, cotton (*Gossypium hirsutum*), soybean (*Glycine max*), peanut (*Arachis hypogaea*), and members of the genus Brassica.

Methods for transforming monocots are well known to those skilled in the art. Transformation and plant regeneration using these methods have been described for a number of crops including, but not limited to, barley (*Hordeum vulgarae*); maize (*Zea mays*); oats (*Avena sativa*); orchard grass (*Dactylis glomerata*); rice (*Oryza sativa*, including indica and japonica varieties); sorghum (*Sorghum bicolor*); sugar cane (*Saccharum sp*); tall fescue (*Festuca arundinacea*); turfgrass species (e.g. species: *Agrostis stolonifera, Poa pratensis, Stenotaphrum secundatum*); wheat (*Triticum aestivum*), and alfalfa (*Medicago sativa*). It is apparent to those of skill in the art that a number of transformation methodologies can be used and modified for production of stable transgenic plants from any number of target crops of interest.

The transformed plants are analyzed for the presence of the genes of interest and the expression level and/or profile conferred by the promoters of the present invention. Those of skill in the art are aware of the numerous methods available for the analysis of transformed plants. For example, methods for plant analysis include, but are not limited to Southern blots or Northern blots, PCR-based approaches, biochemical analyses, phenotypic screening methods, field evaluations, and immunodiagnostic assays.

The seeds of this invention can be harvested from fertile transgenic plants and be used to grow progeny generations of transformed plants of this invention including hybrid plant lines comprising the construct of this invention and expressing a gene of agronomic interest.

The present invention also provides for parts of the plants of the present invention. Plant parts, without limitation, include seed, endosperm, ovule, and pollen. In one embodiment of the present invention, the plant part is a seed.

The following examples are included to demonstrate preferred embodiments of the invention. It should be appreciated that the art is unpredictable, and considerable amount of experimentation may be required even by a person skilled in the art to make and use the claimed inventions. Nonetheless, the kind and amount of experimentation required to make and use the full scope of the subject matter claimed is well within the knowledge and skills of a person with an ordinary level of knowledge and skill in this art to perform without undue experimentation. The techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

This example describes identification and isolation of corn and sorghum HRGP (Silk-1) promoter sequences from rice genomic DNA library.

Publicly known sequences of the HRGP gene (GENBANK ACCESSION:X56010 and AJ131535 for Sorghum and Corn respectively) were used to design inverse PCR primers from 5' end of the sorghum and corn genes. (PCR, A Practical Approach, edited by McPherson M. J.; Quirke P.; and Taylor G. R. pp. 137-145; 1993, Oxford University Press, New York). Appropriate genomic DNA both from corn and from sorghum was digested and re-ligated separately to form circular DNA molecules by using standard molecular biology techniques (Sambrook et al., 2000). Circular Genomic DNA was used to perform inverse PCR to isolate and identify regulatory regions of the HRGP gene from sorghum and corn DNA amplicons by recloning and sequencing (Sambrook, et al., 2000).

Example 2

This example describes construction of plant transformation vector pMON 78354 (FIG. 1), where the corn HRGP promoter was cloned in the proper orientation to express a marker gene β-glucuronidase from E. coli.

The corn HRGP promoter fragment was amplified by using standard inverse PCR reactions as mentioned in Example 1. The resulting amplicon was cloned in a vector by using the InsT/Aclone™ PCR Product Cloning Kit as per the instruction of the manufacturer (Catalog No. K1214, FERMENTAS INC, Hanover, Md.). The cloned HRGP promoter was re-analyzed for its authenticity by restriction analysis and sequenced by well-known methods in the art.

The cloned promoter was removed by using restriction enzymes for cloning in a plant transformation vector. A corn HRGP promoter fragment of the appropriate size was purified by electrophoresis through an agarose gel by well-known methods of molecular biology. Purified promoter DNA with suitable ends was cloned at compatible restricted sites of appropriately digested vector pMON78350 to make a plant transformation vector pMON78354. The plant transformation vector pMON78354, with all of its elements, is shown in FIG. 1. All DNA and vector manipulations were done by standard molecular biology techniques (Sambrook, et al.) using desired enzymes according the manufacturer (Invitrogen, Carlsbad, Calif.).

Example 3

This example describes transformation of a corn plant with the DNA construct pMON78354 to analyze the expression pattern of marker gene β-glucuronidase controlled by corn HRGP promoter.

Transgenic corn was produced by particle bombardment transformation methods as described in U.S. Pat. No. 5,424,412. The vector DNA of plasmid pMON78354 was digested with suitable restriction endonucleases to isolate a plant expression cassette capable of expressing E. Coli β-glucuronidase in corn plants. The desired expression cassette was purified by agarose gel electrophoresis, and then bombarded into 3-5 day pre-cultured, zygotic immature embryos using a Biolistic® (Dupont, Wilmington, Del.) particle gun with purified isolated DNA fragments as per the instruction of manufacturer. The bombarded immature embryos were selected on selection media supplemented with 500 mg/l of paramomycin (Sigma Chemical Co., Saint Louis Mo., Catalog. No, P8692) to regenerate whole plants (Armstrong, C. L., et al.; Maize Genetics Coop Newsletter; 65: 92-93; 1991). Regenerated plants were grown under greenhouse conditions. Fertile seed was collected and planted, and the paramomycin tolerant phenotype was back crossed into commercially acceptable corn germplasm by methods known in the art of corn breeding (Sprague, et al., Corn and Corn Improvement $3^{rd}$ Edition, Am. Soc. Agron. Publ (1988)).

Example 4

This example illustrates the analysis of corn HRGP promoter expression patterns in corn plants. Qualitative and quantitative analysis in desired plant tissue was performed using histochemical and MUG assays (Jefferson, et al. EMBO J.; 6: 3901-3907; 1987).

The MUG assays provide a quantitative analysis of the leaf, embryo, endosperm, and other tissue expression in the transgenic plants. Total protein was extracted from desired plant tissue by dissecting different tissue from transgenic corn plants. Plant tissue from un-transformed plants at the same growth stage was used as negative control. In preparation for the MUG assay, 500 µl of GUS extraction buffer were added to the tissues, and tissues were ground with a teflon pestle in 1.5 ml eppendorf tubes and centrifuged at 10,000 RPM for 5 minutes at 4° C. (Beckman GS-15R). 400 µl of supernatant were transferred to a fresh 96 deep well plate. Extracts in 96 deep well plates were frozen on dry ice and stored at −80° C. until use. The MUG assay consisted of generating a standard curve of activity with a serial dilution of 4-methyl umbelliferone (SIGMA M1381) from 10 pmol to 800 pmol. 5 µl of each extract were added to a flat bottom 96-well plate (Falcon 3872) in duplicate and the plate was preread for blanking the background. 45 µl of assay solution (0.1 M $KPO_4$ pH7.8, 1.0 mM EDTA, 5% glycerol, 10.0 mM DTT, 2 mM 4-methyl umbelliferyl glucuronide Fluka 69602) were added to each well and mixed with the samples by pipetting. The plate was incubated at 37° C. for 1 hour, then stopped by adding 350 µl of 0.2 M Na2CO3 buffer. Fluorescence was measured with excitation at 365 nm and emission at 445 nm using Fluoromax-3 with Micromax Reader (Jobin Yvon Inc., 3880, Park Avenue, Edison, N.J. 08820, USA), with slit width set at excitation 2 nm and emission 3 nm. GUS activity (pmol/h/µg of protein) was calculated based on MUG results and protein results of each sample. Total protein was assayed using a Bio-Rad Protein Assay kit. Serial dilutions of BSA protein from 0.05 mg/ml to 0.5 mg/ml were used for the standard curve. 1.5 µl of extracts were added to flat bottom 96-well plate (Falcon) in duplicate. 300 µl of diluted dye reagent were added and mixed with the samples. The absorbance at 595 nm was measured using KC Junior (Bio-TE, Highland Park, Box: 998, Winooski, Vt. 05404-0998, USA) at room temperature after a 5 minute incubation at room temperature. The MUG analysis demonstrated that the promoter disclosed herein is expressed in various cell types of corn leaf, root, cob, anther, embryo, and endosperm during different developmental stages. Independently transformed corn lines can be selected from the population of plants transformed with the promoters of the present invention that express at different developmental stages of corn leaf, root, cob, anther, embryo, and endosperm. The results of quantitative and qualitative expression analysis are shown in Table 1 and Table 2, respectively.

The results in Table 1 show the quantitative expression pattern caused by the corn promoter of present invention (Table 1) in different tissues of corn plants. These results also indicate that the corn promoter of the present invention is capable of causing expression of a transgene in a variety of tissues. However, the level of expression in different tissues varies. These results clearly suggest that expressing a transgene under the control of the HRGP promoter will result in a differential expression pattern of that gene in the transgenic plant.

In Table 1, GUS activity is reported in terms of pmol of MU/μg of protein/hour. The enzyme blank was observed to give an activity less than 0.1 pmol of MU/μg of protein/hour. Each data point for the V3 to V7 stage is an average of at least two plants. Cold treatment of plants was done by exposing the plant to 15° C. for 24 hours. Plants were desiccated by withholding water until plant moisture content was reduced to 50% as compared to fully hydrated plants. The abbreviations in Table 1 are: DAG—Days After Germination; DAP—Days After Pollination; VT—Tasseling stage; C—coleoptile; R—Root; L—Leaf; V3—three leaf stage; V7—Seven leaf stage; and nd—not determined.

TABLE 1

Quantitative GUS expression analysis.

| Stages | Organ | Inducer | Range | Mean ± SE |
|---|---|---|---|---|
| Imbibed seed | Embryo | — | 13.67-13.67 | 13.67 ± 0.00 |
| Imbibed seed | Endosperm | — | 21.55-50.54 | 36.04 ± 14.49 |
| 3 DAG | Root | — | 20.20-161.59 | 54.51 ± 9.16 |
| V3 | Root | — | 0.10-0.10 | 0.10 ± 0.00 |
| V3 | Root | Cold | nd-nd | nd ± nd |
| V3 | Root | Desiccation | nd-nd | nd ± nd |
| V7 | Root | — | 0.10-0.10 | 0.10 ± 0.00 |
| VT | Root | — | 0.10-0.10 | 0.10 ± 0.00 |
| 3 DAG | Coleoptile | — | 21.12-292.38 | 35.11 ± 7.47 |
| V3 | Leaf | — | 0.10-0.10 | 0.10 ± 0.00 |
| V3 | Leaf | Cold | nd-nd | nd ± nd |
| V3 | Leaf | Desiccation | nd-nd | nd ± nd |
| V7 | Leaf - Mature | — | 0.10-0.10 | 0.10 ± 0.00 |
| V7 | Leaf - Young | — | 0.10-0.10 | 0.10 ± 0.00 |
| VT | Leaf - Mature | — | 0.10-0.10 | 0.10 ± 0.00 |
| VT | Cob | — | 0.10-0.10 | 0.10 ± 0.00 |
| VT | Anther | — | 0.10-0.10 | 0.10 ± 0.00 |
| VT | Silk | — | 54.56-104.58 | 79.57 ± 25.01 |
| 14 DAP | Embryo | — | 38.52-161.15 | 86.00 ± 29.20 |
| 21 DAP | Embryo | — | nd-nd | nd ± nd |
| 35 DAP | Embryo | — | 33.23-366.27 | 105.42 ± 17.87 |
| 7 DAP | Kernel | — | 35.65-232.36 | 75.99 ± 23.10 |
| 14 DAP | Endosperm | — | 30.50-99.92 | 53.88 ± 12.03 |
| 21 DAP | Endosperm | — | nd-nd | nd ± nd |
| 35 DAP | Endosperm | — | 31.94-115.40 | 59.97 ± 12.14 |

The results in Table 2 show the qualitative expression pattern caused by the corn promoter of present invention in different cell types of corn plant. These results also indicate that the corn promoter of the present invention is capable of causing expression of a transgene in a variety of cell types in different tissues. However, the intensity of the blue color in the histochemical assay, at different growth stages, varies in different cell types. The HRGP promoter exhibits expression in silks that could provide unique advantages for making transgenic plants with very special properties. These results clearly suggest that a transgene expressed under the control of the HRGP promoter will have great utility to obtain transgenic plants in which a differential expression pattern of the gene is desired.

In Table 2, cold treatment of plants was done by exposing the plant to 15° C. temperatures for 24 hours. Stable transgenic corn plants were desiccated by withholding water until plant moisture content was reduced to 50% as compared to fully hydrated plants. Abbreviations in Table 2 are: DAG—Days After Germination; DAP—Days After Pollination; VT—Tasseling stage; C—coleoptile; R—Root; L—Leaf; V3—three leaf stage; V7—Seven leaf stage.

TABLE 2

Qualitative GUS expression analysis.

| Stage | Inducers | Tissue | Cell Types where expression is observed |
|---|---|---|---|
| Imbibed seed | — | Seed | No GUS Detected |
| 3 DAG | — | Root | No GUS Detected |
| V3 | — | Root | No GUS Detected |
| V3 | Cold | Root | Not determined |
| V3 | Desiccation | Root | Not determined |
| V 7 | — | Root | No GUS Detected |
| VT | — | Root | No GUS Detected |
| 3 DAG | — | Apical regions | No GUS Detected |
| V3 | — | Leaf | No GUS Detected |
| V3 | Cold | Leaf | Not determined |
| V3 | Desiccation | Leaf | Not determined |
| V7 | — | Leaf - source | No GUS Detected |
| V7 | — | Leaf - sink | No GUS Detected |
| VT | — | Leaf (source) | No GUS Detected |
| VT | — | Leaf (senescence) | No GUS Detected |
| V 7 | — | Node | No GUS Detected |
| V T | — | Node | No GUS Detected |
| V 7 | — | Internode - elongating | No GUS Detected |
| VT | — | Internode - elongated | No GUS Detected |
| V 7 | — | spikelet | No GUS Detected |
| V T | — | spikelet | No GUS Detected |
| V 7 | — | Cob | No GUS Detected |
| V T | — | Cob | Silk |
| 7 DAP | — | Kernel | No GUS Detected |
| 14 DAP | — | Kernel | No GUS Detected |
| 21 DAP | — | Kernel | No GUS Detected |
| 35 DAP | — | Kernel | No GUS Detected |

Example 5

This example illustrates the utility of derivatives of the corn HRGP promoter. Derivatives of the corn HRGP promoter are generated by introducing mutations into the nucleotide sequence of the promoter as disclosed in U.S. Pat. No. 6,747, 189, incorporated herein by reference. A plurality of mutagenized DNA segments derived from the corn HRGP promoter, including derivatives with nucleotides deletions and modifications, are generated and inserted into a plant transformation vector operably linked to a GUS marker gene. Each of the plant transformation vectors are prepared essentially as described in Example 2 except that the full length corn HRGP promoter is replaced by a mutagenized derivative of the promoter. Corn plants are transformed with each of the plant transformation vectors and analyzed for expression of the GUS marker to identify those mutagenized derivatives having promoter activity.

Example 6

This example illustrates the utility of modified promoters derived from the corn HRGP promoter. Fragments of the corn HRGP are generated by designing primers to clone fragments of the native corn promoter. A plurality of cloned fragments of the promoter ranging in size from 50 nucleotides up to about full length are obtained using the methods of Example 1 except that the primers are designed for fragments instead of the full length promoter. 3' fragments from the 3' end of the corn HRGP comprising the CAAT and TATA boxes and random fragments of about 50, 100, 150, 200, 250, 300, 350, 400, 450, 500, 550, 600, 650, 700, 750, 800, 850, 900, 950, 1000, 1050, 1100, 1150, 1200, 1250, 1300, 1350, and 1400 nucleotides in length from various parts of the corn HRGP promoter are obtained and inserted into a plant transformation vector operably linked to a GUS marker gene. Each of the plant transformation vectors are prepared essentially as described in Example 2, except that the full length corn HRGP promoter is replaced by a fragment of the promoter or a combination of a 3' fragment and a random fragment. Corn plants are transformed with each of the plant transformation vectors and analyzed for expression of the GUS marker to identify those fragments having promoter activity.

Example 7

This example illustrates the identification and isolation of corn and sorghum HRGP promoters from organisms other than corn and sorghum using the native corn and sorghum HRGP promoter DNA sequences of SEQ ID NO:1 or SEQ ID NO:2 and fragments to query genomic DNA from other organisms in publicly available nucleotide databases, including GENBANK. DNA sequences ranging of at least 700 nucleotides and at least 85% identity to sequences within SEQ ID NO:1 or SEQ ID NO:2 are identified as being part of a putative HRGP promoter. The full promoters may be cloned and inserted into a plant transformation vector that is used to transform corn plants essentially as illustrated in Example 6 to verify promoter activity and HRGP promoter expression patterns.

I claim:

1. An isolated DNA molecule having promoter function and comprising the SEQ ID NO:1.

2. A recombinant DNA expression cassette having a promoter comprising DNA of claim 1 operably linked to DNA to be transcribed.

3. The recombinant DNA expression cassette of claim 2, wherein said DNA to be transcribed is a gene of agronomic interest.

4. The recombinant DNA expression cassette of claim 2, wherein said DNA to be transcribed is a marker gene.

5. A transgenic plant having in its genome a recombinant DNA expression cassette of claim 2.

6. The transgenic plant of claim 5, wherein said DNA to be transcribed transcribes to RNA imparting gene suppression of at least one gene in said transgenic plant.

7. A transgenic seed of a transgenic plant of claim 5.

8. Transgenic seed of a transgenic plant of claim 5, wherein said transgenic plant is selected from the group consisting of corn, soybean, cotton, wheat, rice, and canola.

9. A part of the transgenic plant of claim 5.

10. The part of claim 9, further defined as a cell of the transgenic plant of claim 8.

* * * * *

UNITED STATES PATENT AND TRADEMARK OFFICE
CERTIFICATE OF CORRECTION

| | | |
|---|---|---|
| PATENT NO. | : 7,390,655 B2 | Page 1 of 1 |
| APPLICATION NO. | : 11/387036 | |
| DATED | : June 24, 2008 | |
| INVENTOR(S) | : Brendan Hinchey | |

It is certified that error appears in the above-identified patent and that said Letters Patent is hereby corrected as shown below:

On the Title Page; insert item [63] --Provisional application No. 60/663,817, filed on March 21, 2005.-- under Related U.S. Application Data.

In claim 1, column 13, line 3, delete "the".

Signed and Sealed this

Sixth Day of September, 2011

David J. Kappos
*Director of the United States Patent and Trademark Office*